United States Patent
Lipschutz et al.

(10) Patent No.: US 9,155,634 B2
(45) Date of Patent: Oct. 13, 2015

(54) SYSTEMS AND METHODS OF MYOELECTRIC PROSTHESIS CONTROL

(75) Inventors: Robert Lipschutz, Chicago, IL (US); Dennis Tkach, Chicago, IL (US); Blair Lock, Chicago, IL (US); Levi Hargrove, Chicago, IL (US); Todd Kuiken, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 13/587,755

(22) Filed: Aug. 16, 2012

(65) Prior Publication Data

US 2013/0046394 A1 Feb. 21, 2013

Related U.S. Application Data

(60) Provisional application No. 61/524,209, filed on Aug. 16, 2011.

(51) Int. Cl.

| | |
|---|---|
| *A61F 2/70* | (2006.01) |
| *A61F 2/80* | (2006.01) |
| *A61F 2/72* | (2006.01) |
| *A61F 2/78* | (2006.01) |
| *A61F 2/60* | (2006.01) |
| *A61F 2/68* | (2006.01) |

(52) U.S. Cl.
CPC .............. *A61F 2/72* (2013.01); *A61F 2/7812* (2013.01); *A61F 2/60* (2013.01); *A61F 2/68* (2013.01); *A61F 2002/607* (2013.01); *Y10T 29/49224* (2015.01)

(58) Field of Classification Search
CPC .................. A61F 2/72; A61F 2/7812
See application file for complete search history.

(56) References Cited

U.S. PATENT DOCUMENTS

| | | | |
|---|---|---|---|
| 5,213,715 A | 5/1993 | Patterson et al. | |
| 5,258,037 A | 11/1993 | Caspers | |
| 5,376,132 A | 12/1994 | Caspers | |
| 5,413,611 A | 5/1995 | Haslam, II et al. | |
| 5,443,525 A | 8/1995 | Laghi | |
| 5,507,834 A | 4/1996 | Laghi | |
| 5,785,040 A | 7/1998 | Axelgaard | |
| 5,830,237 A * | 11/1998 | Kania | 623/37 |

(Continued)

FOREIGN PATENT DOCUMENTS

| | | |
|---|---|---|
| DE | 102007035409 A1 | 1/2009 |
| EP | 2737878 A1 | 4/2014 |
| WO | WO03082103 | 10/2003 |

OTHER PUBLICATIONS

L. Beckmann et al, Characterization of textile electrodes and conductors using standardized measurement setups, Physiol. Meas. 31 (2010) 233-247.

(Continued)

*Primary Examiner* — Jacqueline Woznicki
(74) *Attorney, Agent, or Firm* — Polsinelli PC

(57) ABSTRACT

Embodiments of the invention provides myoelectric prosthesis control system that include a gel liner that has a plurality of layers and a plurality of leads at least partially positioned between the plurality of layers. In addition, a plurality of electrodes can be coupled to the leads and portions of the electrodes can also be positioned between the plurality of layers. At least some of the electrodes can include an electrode pole that is configured to contract the residual limb to detect electromyographic signals.

19 Claims, 6 Drawing Sheets

(56) References Cited

U.S. PATENT DOCUMENTS

| | | | |
|---|---|---|---|
| 6,852,269 B2 | 2/2005 | Eberle et al. | |
| 6,970,731 B1 | 11/2005 | Jayaraman et al. | |
| 7,412,281 B2 | 8/2008 | Shen et al. | |
| 7,522,951 B2 | 4/2009 | Gough et al. | |
| 7,966,052 B2 | 6/2011 | DeFusco et al. | |
| 8,024,023 B2 | 9/2011 | Tolvanen | |
| 8,170,656 B2 | 5/2012 | Tan et al. | |
| 8,591,599 B1 | 11/2013 | Kaliki et al. | |
| 2005/0101693 A1 | 5/2005 | Arbogast et al. | |
| 2005/0119701 A1 | 6/2005 | Lauter et al. | |
| 2006/0282175 A1* | 12/2006 | Haines et al. | 623/24 |
| 2007/0021841 A1 | 1/2007 | Al-Temen et al. | |
| 2007/0078324 A1 | 4/2007 | Wijesiriwardana | |
| 2007/0093134 A1 | 4/2007 | Marmaropoulos et al. | |
| 2008/0045808 A1 | 2/2008 | Hassonjee et al. | |
| 2008/0161893 A1 | 7/2008 | Paul et al. | |
| 2009/0076362 A1 | 3/2009 | Jaatinen | |
| 2009/0112079 A1 | 4/2009 | Hassonjee et al. | |
| 2009/0132056 A1 | 5/2009 | Kania | |
| 2009/0216339 A1 | 8/2009 | Hanson et al. | |
| 2009/0277528 A1 | 11/2009 | Shen et al. | |
| 2009/0292193 A1 | 11/2009 | Wijesiriwardana | |
| 2010/0004524 A1 | 1/2010 | Yuen | |
| 2010/0114238 A1 | 5/2010 | Muccio | |
| 2010/0114273 A1 | 5/2010 | Muccio | |
| 2010/0137702 A1 | 6/2010 | Park et al. | |
| 2010/0185076 A1 | 7/2010 | Jeong et al. | |
| 2010/0318195 A1 | 12/2010 | Kettwig et al. | |
| 2010/0324405 A1 | 12/2010 | Niemi et al. | |
| 2011/0270414 A1 | 11/2011 | Laghi et al. | |
| 2012/0190989 A1 | 7/2012 | Kaiser et al. | |
| 2012/0253475 A1 | 10/2012 | Kelley | |
| 2012/0296445 A1 | 11/2012 | Leiniger et al. | |
| 2013/0046392 A1 | 2/2013 | Venu et al. | |
| 2013/0331950 A1 | 12/2013 | Laghi et al. | |

OTHER PUBLICATIONS

D. Farina et al, High-Density EMG E-Textile Systems for the Control of Active Prostheses, 32nd Annual International Conference of the IEEE EMBS, Buenos Aires, Argentina, Aug. 31-Sep. 4, 2010 3591-3593.

D. Kowalk et al, Technical Note, Abduction-Adduction Moments at the Knee During Stair Ascent and Descent, J. Biomechanics, vol. 29, No. 3 (1996) 383-388.

M. Mestrovic et al, Preliminary study of dry knitted fabric electrodes for physiological monitoring, ISSNIP 2007 601-606.

J. Taelman et al, Textile Integrated Contactless EMG Sensing for Stress Analysis, Proceedings of the 29th Annual International Conference of the IEEE EMBS, Aug. 23-26, 2007 3966-3969.

Z. Zhang et al, Usability Analysis of Textile Sensors in Control of Multifunction Myoelectric Prostheses (2010).

Jet Propulsion Laboratory, Biosleeve: Multi-electrode EMG Sleeve Human-Machine Interface, at http://www-robotics.jpl.nasa.gov/tasks/showTask.cfm?TaskID=103&tdaID=888883.

Ossur pp. 1-2, Iceross Original Locking Liner. Verified by the Wayback Machine Dec. 21, 2010.

Dupont Tyvek Products. Verified by the Wayback Machine Aug. 6, 2012.

Daly. Clinical Application of Roll-on Sleeves for Myoelectrically Controlled Transradial and Transhumeral Prostheses. Journal of Prosthetics and Orthotics. vol. 12, No. 3. pp. 88-91.

ABB. Silicone Rubber Product Information. May 15, 2005.

* cited by examiner

SYSTEMS AND METHODS OF MYOELECTRIC PROSTHESIS CONTROL

CROSS-REFERENCE TO RELATED APPLICATIONS

The present application claims priority to U.S. Provisional application No. 61/524,209 filed on Aug. 16, 2011, the entire contents and disclosure of which are herein incorporated by reference.

STATEMENT REGARDING FEDERALLY SPONSORED RESEARCH

This invention was made with Government support under Grant Nos. W81XWH-09-2-0020 and W81XWH-10-2-0033 both awarded by the Defense Advanced Research Projects Agency as well as under a subcontract from John Hopkins Applied Physics Lab under Grant No. 908090 awarded by the Defense Advanced Research Projects Agency. The Government has certain rights in the invention.

FIELD

This document generally relates to the field of powered prosthetic devices, and in particular to the embedding of conductive fabric electrodes and leads in a gel liner to allow detection of myoelectric signals for control of a prosthetic device.

BACKGROUND

Limb amputation can result in profound disability, for which the most effective treatment is replacement of the missing limb with a prosthetic device. Effective options for treatment include body-powered prostheses, which rely on Bowden cables to translate gross body movements into control signals; and myoelectric prostheses, which are controlled by myoelectric signals (also called electromyographic or EMG signals) received from residual muscles of the individual with an amputation. Myoelectric signals are small electrical signals that propagate through a muscle as a result of nerve impulses, which causes contraction of the muscle fibers. Control of myoelectric prostheses relies on the detection of these signals through electrodes on the skin surface such that the voluntary contraction of a muscle can be used to actuate a specific intended movement in a prosthetic device attached to the individual with an amputation. The small voltage detected (typically 10 μV-1 mV) is conditioned electronically to render it suitable for actuation and control of the required motors in the prosthetic device. Typically, signal conditioning may be provided at the electrode contact site or within a separate electronic processing system. In either case, signals must be transmitted from the electrode to the control system of the prosthesis via wires or leads.

Prosthetic devices controlled by myoelectric signals have been under development since the late 1950s and have found a prominent place in the commercial market. Myoelectric control eliminates much of the prominent and uncomfortable harnessing necessary for body-powered control and reduces the effort required by the wearer to actuate the limb; however, use of a myoelectric device requires physical contact between the electrode and the skin surface.

Individuals with amputations may be fitted with a conventional gel liner, which is a soft insert placed between the residual limb and prosthetic socket that provides cushion to the limb and helps suspend the prosthesis. Some conventional gel liners may be constructed from a variety of materials such as urethane, silicone, or thermoplastic elastomers and are configured to provide a tight-fitting, compliant interface between the residual limb and the hard outer socket. Gel liners can be easy to roll onto the residual limb and provide increased comfort. In addition, some or all relative movement—and resulting friction—between the limb and gel liner may be prevented, thereby protecting the skin on the residual limb from possible abrasion or breakdown.

SUMMARY

In one embodiment, a myoelectric prosthesis control system may include a gel liner that may have a plurality of layers and can be configured to be worn over a residual limb. In one embodiment, a plurality of leads can be at least partially positioned between the plurality of layers and coupled to a plurality of electrodes. In one embodiment, at least a portion of the plurality of electrodes can also be positioned between the plurality of layers. Moreover, each of the plurality of electrodes can include an electrode pole that may be configured to contact the residual limb when the gel liner is worn over the residual limb. The electrode poles can be configured to detect electromyographic signals and at least some of the plurality of electrodes and at least some of the plurality of leads can be manufactured from a compliant conductive material.

In another embodiment, a myoelectric prosthesis control system may include a gel liner that may have an inner layer and an outer layer and can be configured to be worn over a residual limb. In one embodiment, a plurality of leads, which may be fabricated from a conductive fabric, can be positioned between the inner layer and the outer layer. A plurality of electrodes can be coupled to the plurality of leads at least partially supported by the gel liner. The plurality of electrodes may be configured to detect electromyographic signals. In some embodiments, a distal end connector can be embedded within the gel liner.

In yet another embodiment a method is provided for making a gel liner for use with a myoelectric prosthesis control system. The method can include assembling an outer layer from a non-conductive fabric and fabricating at least one electrode and at least one lead from a compliant conductive material. In one embodiment, at least one electrode and at least one lead can be coupled to the outer layer. The method can further provide coating at least a portion of the outer layer with a layer of a thermoplastic elastomer so that the layer of thermoplastic elastomer faces the residual limb when the gel liner is worn and so that at least one lead is positioned between outer layer and the layer of the thermoplastic elastomer. Moreover, in one embodiment, the layer of thermoplastic elastomer can be coated over the outer layer so that at least one electrode at least partially protrudes from the layer of the thermoplastic elastomer.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figures 1, 3:
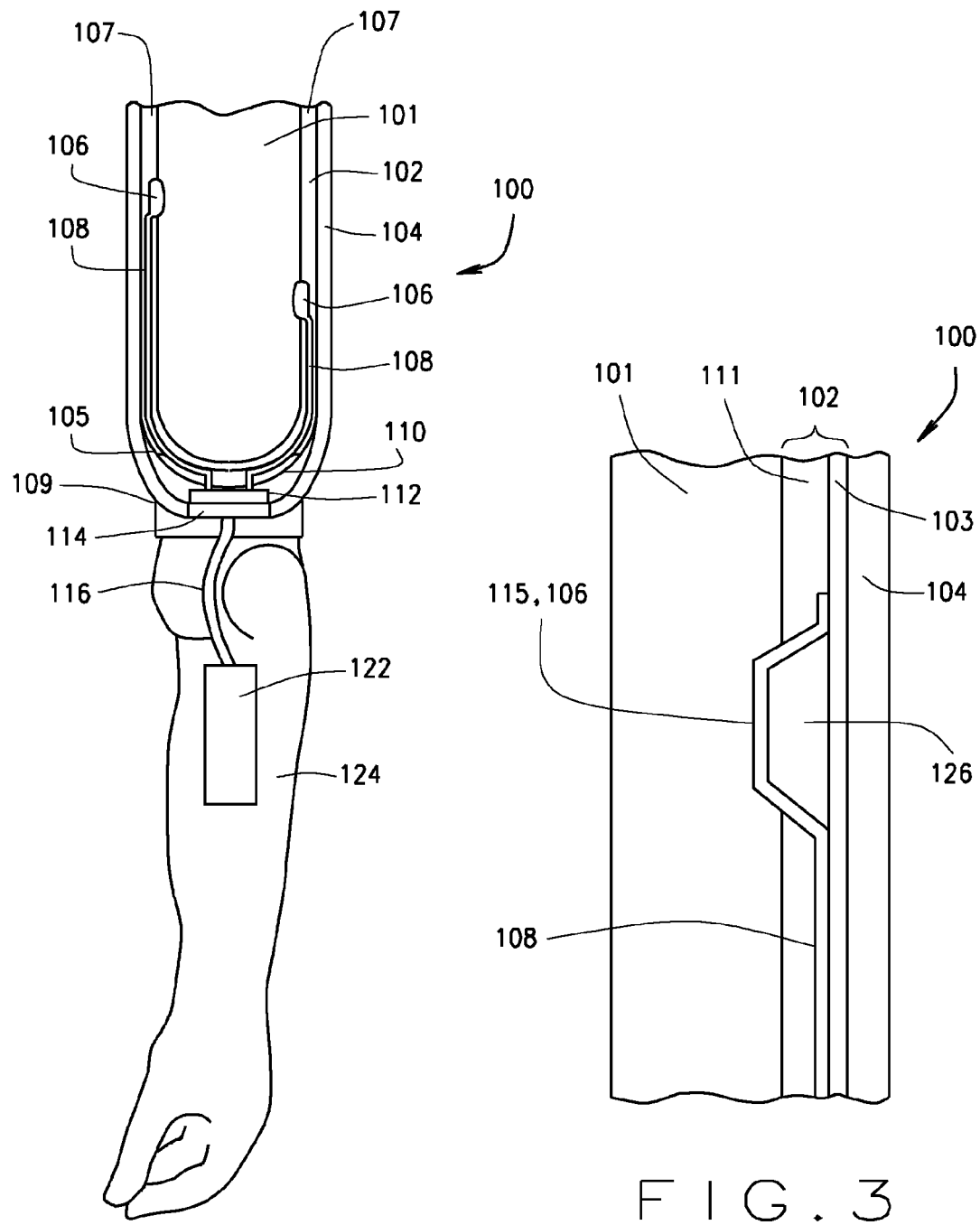
FIG. 1 is a simplified illustration of an embodiment of a myoelectric prosthesis control system.
FIG. 3 is an enlarged simplified illustration a gel liner according to one embodiment.

Referring to the drawings, embodiments of the myoelectric prosthesis control system are illustrated and indicated as 100, 200, 300, and 400 in FIGS. 1-13. In one embodiment, the prosthesis control system 100 can include a prosthesis 124 that is fitted to an individual (not shown). More specifically, the prosthesis 124 can be configured to operate as a myoelectrically-controlled device that can be professionally custom fit for the individual. For example, in one embodiment, the prosthesis 124 can be configured as a prosthetic limb for an individual with a shoulder disarticulation. In other embodiments, the prosthesis 124 can be configured differently, such as a prosthetic limb for individuals with transradial and/or transhumeral amputations. In yet other embodiments, the prosthesis 124 can be configured for individuals with amputations or disarticulations of other limbs.

Referring to FIG. 1 in some embodiments, the myoelectric prosthesis control system 100 can be configured for use by an individual with a transhumeral amputation so that the prosthesis 124 is configured to function as a lower portion of an arm of the individual with the amputation. For example, the prosthesis 124 can be coupled to a prosthesis socket 104 that is configured to receive at least a portion of a residual limb 101. The prosthesis socket 104 can be made from a polymer (e.g., a rigid or stiff polymer), such as a thermoset and/or a thermoplastic material, to provide support for the connection between the prosthesis 124 and the residual limb 101. In some embodiments, the prosthesis socket 104 can be custom fit for the individual who will wear the prosthesis socket 104 and the prosthesis 124 by a technician or a prosthetist. Moreover, the prosthesis socket 104 can be coupled to the prosthesis 124 after being custom fit to the individual so that the individual dons and doffs the prosthesis 124 and the prosthesis socket 104 at the same time.

In some embodiments, the myoelectric prosthesis control system 100 includes a gel liner 102. The gel liner 102 may be configured to be worn by the individual between the residual limb 101 and the prosthesis socket 104. More specifically, the gel liner 102 can be worn over at least a portion of the residual limb 101 to reduce friction between the prosthetic socket 104 and skin (not shown) of the residual limb 101 leading to increased comfort for the individual wearing the gel liner 102. Further, the gel liner 102 can include a distal end 105 and a proximal end 107. For example, the gel liner 102 can be fitted on the residual limb 101 so that the distal end 105 is closer to the prosthesis 124 and the proximal end 107 is further from the prosthesis 124 (e.g., closer to a remainder of the body of the individual wearing the prosthesis 124).

Many conventional myoelectric prostheses may be fit with a rigid, thermoplastic or laminated prosthesis socket 104, which may include conventional electrodes. This conventional configuration may require additional harnessing to achieve proper attachment (i.e., suspension) of the prosthesis socket 104, but may be uncomfortable to the individual using the prosthesis 124, despite a prosthetist's best efforts to mold the prosthesis socket 124 to the individual's limb. Furthermore, the conventional configuration may suffer from a loss of electrode 1061 residual limb 101 contact due to repositioning of the residual limb 101 during activities that may require mid-line prehension and lifting. The fit of the gel liner 102 to the residual limb 101 can at least partially eliminate the loss of contact between the residual limb 101 and the electrodes 106 embedded within the gel liner 102, which makes myoelectric control of the prosthesis 124 more robust.

Figure 2:
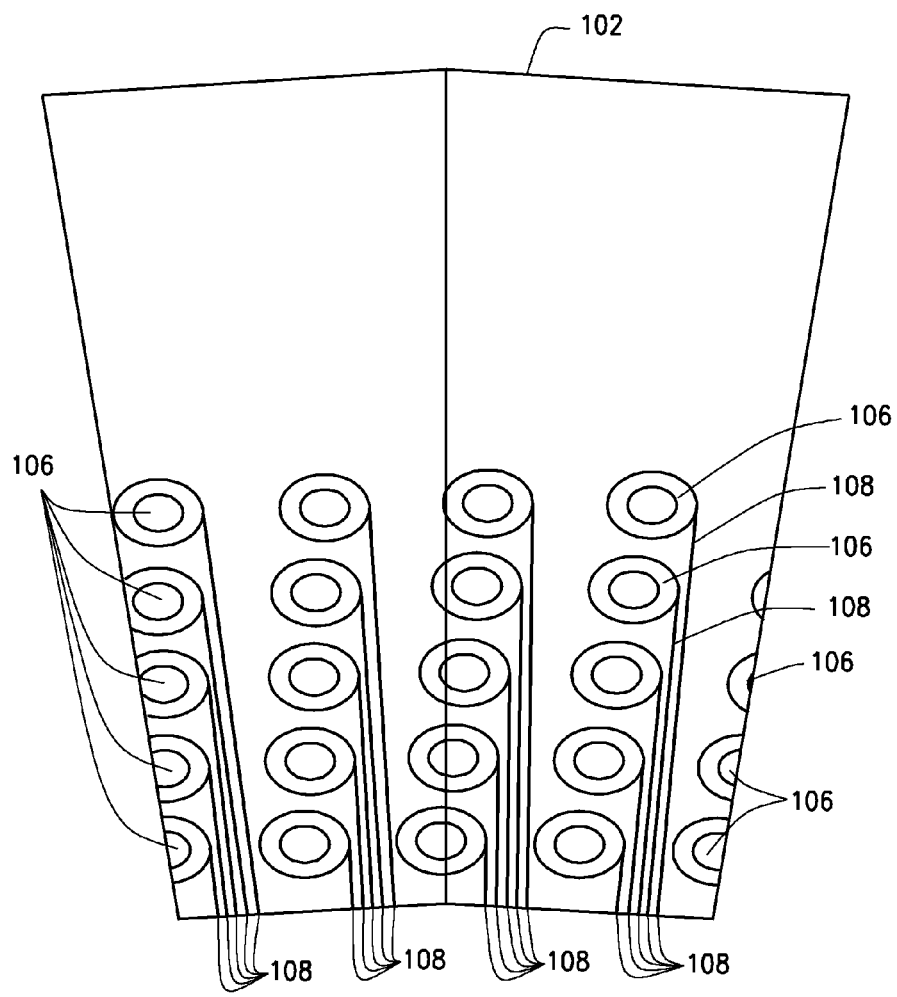
FIG. 2 is a simplified illustration of a portion of a gel liner according to an embodiment.

Moreover, in one embodiment, the gel liner 102 can include at least one electrode 106 and at least one lead 108. For example, the gel liner 102 can include a plurality of electrodes 106 and a plurality of leads 108, as shown in FIGS. 1 and 2. In one embodiment, the electrodes 106 and leads 108 can be made from one or more compliant (e.g., relatively flexible) conductive materials. For example, in some embodiments, at least some of the electrodes 106 and at least some of the leads 108 may be made of a conductive fabric (e.g., a silver-impregnated material). Furthermore, at least one lead 108 can couple each electrode 106 to a signal-conditioning electronics module 112. More specifically, the electrodes 106 can be configured to capture electromyographic ("EMG") signal data from the residual limb 101 and transmit at least a portion of the EMG signal data to the signal-conditioning electronics module 112. Particularly, the signal-conditioning electronics module 112 can be coupled to and/or supported by the gel liner 102 at a position substantially adjacent to the distal end 105 of the gel liner 102. Accordingly, at least some of the leads 108 may pass through and/or exit the gel liner 102 at a position substantially adjacent to the distal end 105.

In some embodiments, the prosthesis socket 104 can include a socket interface 114. For example, the socket interface 114 may be positioned at a distal end 109 of the prosthesis socket 104. In other embodiments, the socket interface 114 can be positioned in any other location within the prosthesis socket 104 or adjacent to or integral with the prosthesis 124 or prosthesis socket 104. In one embodiment, the socket interface 114 may be in communication with the signal-conditioning electronics module 112. As a result, the EMG signal data received from the electrodes 106 through the leads 108 can be transmitted to the socket interface 114 via the signal-conditioning electronics module 112. In one embodiment, the socket interface 114 can be coupled to the signal-conditioning electronics module 112; however, in some embodiments, the socket interface 114 and the signal-conditioning electronics module 112 can be in operative communication via a wired or a wireless connection.

Moreover, in some embodiments, the connection between the signal-conditioning electronics module 112 and the socket interface 114 can be reversible. For example, the individual donning the prosthesis 124 can reconnect the signal-conditioning electronics module 112 and the socket interface 114 each time the individual attaches the prosthesis 124. Conversely, each time the individual removes the prosthesis 124, the removal of the residual limb 101 from within the prosthesis socket 104 can break the connection between the signal-conditioning electronics module 112 and the socket interface 114.

In one embodiment, the socket interface 114 can route the EMG signal data to elements of the prosthesis 124 for use in controlling movement of the prosthesis 124. The prosthesis 124 can include a prosthesis control module 122 that is in operative communication with the socket interface 114. In one embodiment, the socket interface 114 can be in operative communication with the prosthesis control module 122 via one or more wires or cables 116. In some embodiments, the socket interface 114 can be wirelessly associated with the prosthesis control module 122. Accordingly, EMG signal data can be transmitted from the gel liner 102 to the signal-conditioning electronics module 112, which can then transmit data to the socket interface 114 and the prosthesis control module 122. As a result, one or more of the previously mentioned components can process the EMG signal data to control movement of the prosthesis 124 in accordance with the EMG signal data gathered by one or more of the electrodes 106.

In addition, some embodiments of the myoelectric prosthesis control system 100 may provide the individual with the benefits of a conventional gel liner—including increased comfort, EMG signal noise reduction, and improved suspension—while retaining the advantages of myoelectric control. Unlike conventional gel liners, the myoelectric prosthesis control system 100 is configured to enable the electrodes 106 to be incorporated within the gel liner 102 without compromising the function and robustness of the gel liner 102. For example, in order to incorporate electrodes 106 and leads 108 so that the electrodes 106 make contact with the residual limb 101 for myoelectric control while using a conventional gel liner, an individual would be required to cut one or more holes through the conventional gel liner, thereby compromising the structural integrity of the conventional gel liner.

Other conventional configurations can include snap-electrodes that pierce the conventional gel liner. With the conventional snap-electrode configuration, the individual would be required to don the conventional liner, and then prior to donning the prosthesis 124, attach the snap-electrodes to leads originating from the prosthesis 124 and/or the prosthesis socket 104. This conventional process can be difficult and cumbersome for an individual with an upper extremity amputation to manage the connection of the snap-electrodes to the leads. Moreover, the large numbers of leads and other wires necessary for operations related to the conventional snap-electrode configuration can be susceptible to breakage or deterioration over time. By incorporating compliant, conductive electrodes 106 and leads 108 into the gel liner 102, the electrodes 106 and leads 108 and the gel liner 102 can undergo multiple iterations of the donning and doffing process without significant structural fatigue or failure of some or all of the previously mentioned elements. It should be noted that the myoelectric prosthesis control system 100 may be contained within the gel liner 102 and prosthesis socket 104 with no exposed external wires, thereby allowing for ease of use with minimal risk of damage to the components of the myoelectric prosthesis control system 100. Moreover, little to no manual connection of the leads 108 is required, and few or no external wires are involved.

Moreover, some or all of the electrodes 106 may be used in bipolar or monopolar configurations. In some embodiments, electrodes 106 can be applied in a consistent location over specific muscle sites and remain stationary during the wearing of the gel liner 102. To accomplish successful myoelectric control, electrodes 106 may generally be applied over an antagonistic muscle pair (e.g., biceps and triceps). Keeping the electrodes 106 stationary during wear prevents additional noise from being introduced into the EMG signal data and maintains a consistent control signal for optimal function of the prosthesis 124.

More specifically, some embodiments of the myoelectric prosthesis control system 100 retain some or all the benefits of a conventional gel liner, including comfort and improved suspension, while providing the individual using the prosthesis 124 with the advantages of myoelectric control. For example, the gel liner 102 provides one or more advantages with respect to conventional gel liners in multiple aspects. First, by using electrodes 106 and leads 108 that may be fabricated from materials with similar compliance properties to the gel liner 102, the risk of damage to the integrity of the gel liner 102 can be at least partially reduced because of the reduced risk of localized stress and fatigue fractures originating from compromised gel liners and non-compliant conventional electrodes and leads.

Figure 5:
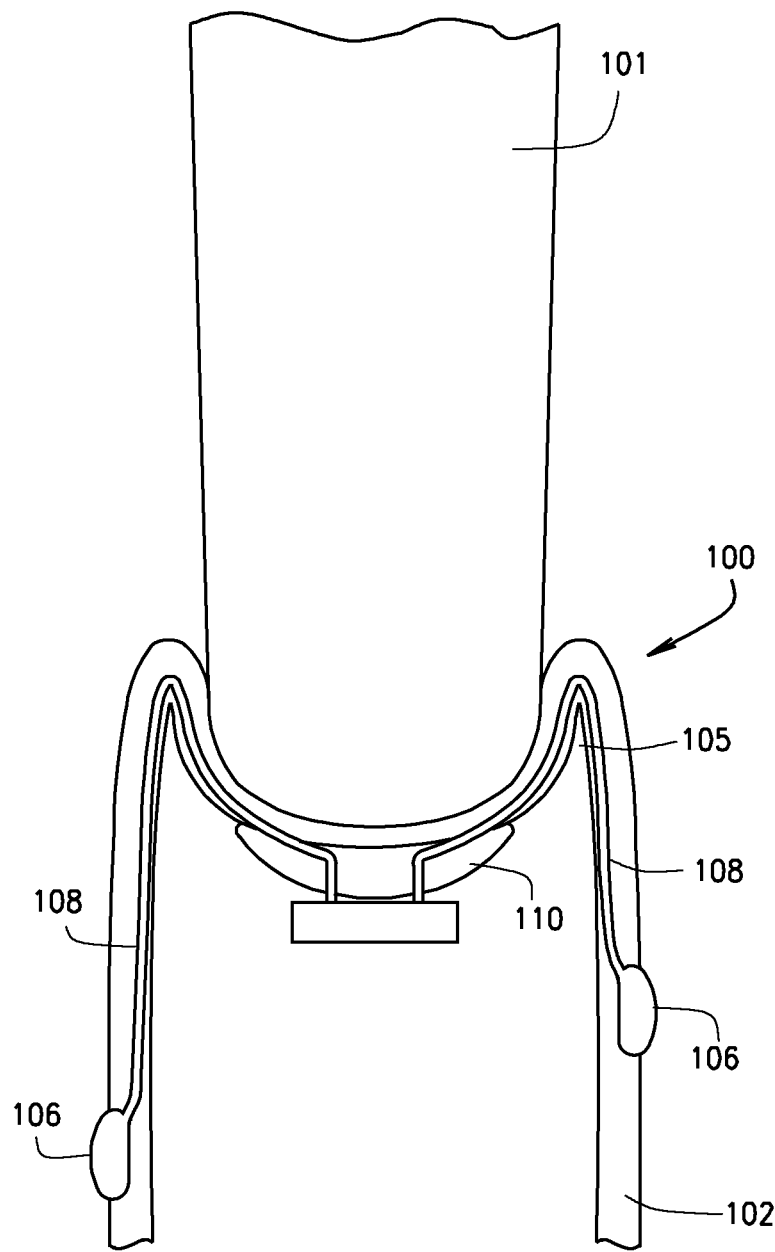
FIG. 5 is a simplified illustration of a portion of the myoelectric prosthesis control system of FIG. 1.

Referring to FIG. 5, when the gel liner 102 is donned, the gel liner 102 may be inverted and the distal end 105 of the gel liner 102 placed in contact with the residual limb 101. After positioning the gel liner 102, the individual may then roll the gel liner 102 onto the residual limb 101. As previously mentioned, the leads 108 and electrodes 106 may be made from a flexible conductive material, such as a fabric, which can eliminate the problem of wire breakage because of the repeated bending as the gel liner 102 is donned and doffed. In addition, by being at least partially embedded in the inner layer 111 (not shown in FIG. 5), damage to leads 108 and electrodes 106 from lateral movement between the inner layer 111 and the outer layer 103 (not shown in FIG. 5), or between residual limb 101 and gel liner 102, is reduced or prevented.

In addition, one or more leads 108 at least partially positioned within the gel liner 102 can route EMG signal data from the gel liner 102 to downstream electronics (e.g., the signal-conditioning electronics module 112, the socket interface 114, the prosthesis control module 122, etc.) without the need for some or any external wires or leads. This enables the individual using the myoelectric prosthesis control system 100 to use the gel liner 102 in a "plug-and-play" manner without the need to manage or connect a wire harness or other difficult-to-manage electronics systems. The leads 108 may also be shielded from the environment and possible damage by being at least partially positioned within the gel liner 102. Overall, the gel liner 102 can reduce the time and complexity associated with fitting a myoelectric-controlled prosthesis 124 to an individual in need of the prosthesis 124. The myoelectric prosthesis control system 100 can provide a self-contained, non-intrusive avenue for acquiring EMG signal data for myoelectric-controlled prostheses 124 in an efficient and cost-effective manner, thereby taking advantage of the added benefits of conventional gel liner technology.

Figure 4:
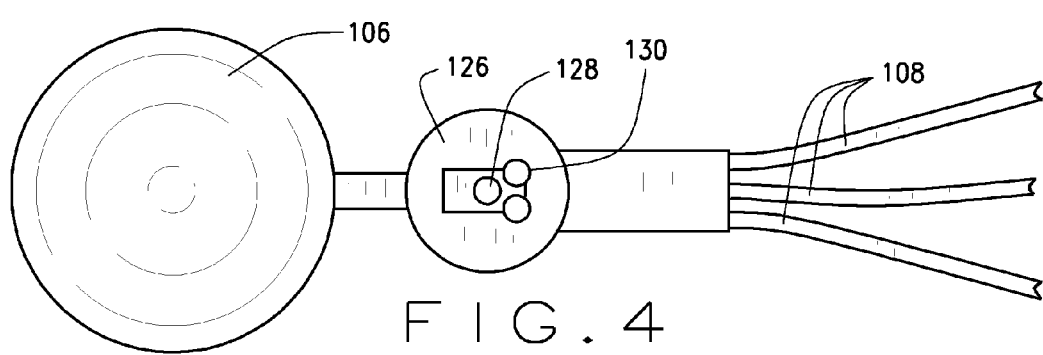
FIG. 4 is a top view of an embodiment of an electrode and lead fabricated from conductive fabric.
Figure 6:
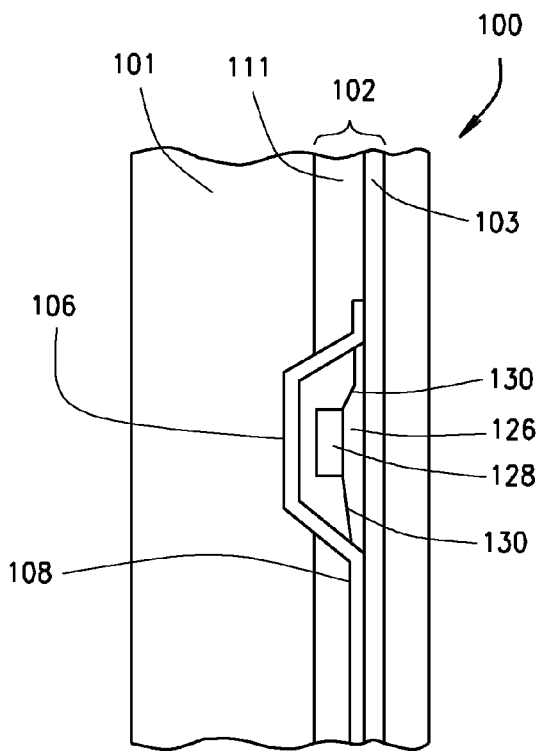
FIG. 6 is an enlarged simplified illustration showing one embodiment of the gel liner.

Referring to FIGS. 3 and 6, one embodiment of the gel liner 102 may include a plurality of layers. For example, the gel liner 102 may include an outer layer 103 and an inner layer 111. More specifically, in one embodiment, when the user wears the gel liner 102, the outer layer 103 can be closer to the prosthesis socket 104 and the inner layer 111 can be immediately adjacent to the residual limb 101. In one embodiment, the outer layer 103 may be made from a commercially available fabric and the inner layer 111 may be made of a thermoplastic elastomer ("TPE") of varying thickness. As previously mentioned, in one embodiment a conductive fabric may be used in the assembly of the electrodes 106 and the leads 108. For example, at least a portion of the electrodes 106 and the leads 108 can be formed from a contiguous piece of conductive fabric (e.g., a single piece of conductive fabric), such as a silver-impregnated fabric. More specifically, as shown in FIGS. 3 and 4, a portion of the fabric is cut to a suitable or desirable size and shape (e.g., a substantially circular configuration, as shown in FIGS. 3 and 4) to form the electrode 106. In addition, using the same fabric, one or more leads 108 can also be formed so that the electrodes 106 are integral with the leads 108. The electrodes 106 and leads 108 may be fabricated from different compliant conductive materials (e.g., different conductive fabrics), which may provide advantages in conductivity, EMG signal noise reduction, longevity, etc. Additionally, in some embodiments, the electrodes 106 and leads 108 may be made from the same or a similar conductive material (e.g., silver-impregnated fabric), but coupled together via an adhesive or other coupling method, such as sewing.

Referring back to FIG. 3, at least some of the electrodes 106 and leads 108 can be coupled to and/or supported by portions of the gel liner 102. For example, the electrodes 106 and the leads 108 can be attached to the outer layer 103 of the gel liner 102 prior to the addition of the inner layer 111. In one embodiment, the electrodes 106 and leads 108 can be coupled to the outer layer 103 using an adhesive (e.g., a fabric glue) or any other suitable coupling method capable of retaining the electrodes 106 and leads 108 in relation to the outer layer 103 (e.g., sewing).

In some embodiments, the gel liner 102 can comprise a backing material 126. For example, the backing material 126 may be placed between at least some of the electrodes 106 and the outer layer 103. More specifically, the backing material 126 can be configured and arranged to raise at least some of the electrodes 106 through a surface of the inner layer 111 to enable contact between the residual limb 101 and the electrodes 106. In some embodiments, the backing material 126 can have a compliant or flexible composition so that during wear of the gel liner 102, the backing material 126 can absorb and transfer mechanical stresses and reduce the likelihood of damage to the electrodes 106 and injury to the individual wearing the gel liner 102. For example, in one embodiment, the backing material 126 can be a silicone-containing material.

In one embodiment, the inner layer 111 can be coupled to the outer layer 103 after positioning and attaching the electrodes 106, the leads 108, and the backing material 126. More specifically, in some embodiments, the inner layer 111 (e.g., TPE) can be applied to or coated over the outer layer 103, the leads 108, and some portions of the electrodes 106. For example, the inner layer 111 can be coated over some or the entire outer layer 103 so that the leads 108 and portions of the electrodes 106 are positioned between the inner layer 111 and the outer layer 103.

As previously mentioned, in some embodiments, TPE can be used as the inner layer 111. As a result, the inner layer 111 can be re-contoured to the shape of the residual limb 101 after curing of the TPE of the inner layer 111. More specifically, TPEs are generally copolymers or physical mixes of polymers (e.g., plastics and rubber) that include both thermoplastic and elastomeric properties to provide stable yet flexible support for the gel liner 102. In some embodiments, silicone may be used as the inner layer 111. In yet other embodiments, the inner layer 111 can be made from any other suitable nonconductive material.

Moreover, the backing material 126 can be configured and positioned beneath the electrodes 106 so that some portions of the electrodes 106 protrude from the inner layer 111 to contact the residual limb 101. For example, an electrode pole 115 can protrude from the inner layer 111 to contact the residual limb 101 to gather EMG signal data. Particularly, the backing material 126 can function to help in retaining the electrode pole 115 in contact with the residual limb 101 so that the electrodes 106 can gather high-quality EMG signal data.

In some embodiments, the gel liner 102 may be disposable and can be used for a predetermined time period (e.g., approximately six months). In some embodiments, the myoelectric prosthesis control system 100 can use less expensive electrodes 106 and leads 108, which are similarly disposable. This feature also supports the option of mass production of generic gel liners 102, which would further reduce costs. For example, the signal-conditioning electronics module 112 may be removed via a pass-through screw 118 and disconnection of the leads 108, thereby allowing for reuse of the signal-conditioning electronic module 112 with a new gel liner 102.

Referring to FIGS. 4 and 6, in some embodiments, the backing material 126 can include one or more sets of electronic devices. For example, the backing material 126 can include signal-conditioning electronics 128. In one embodiment, the signal-conditioning electronics 128 can be configured to initially condition, augment, or otherwise process the EMG signal data received by the electrodes 106 for downstream use in controlling movement of the prosthesis 124. The signal-conditioning electronics 128 can be positioned within the backing material 126 and electrically coupled to the electrodes 106 via one or more backing leads 130. As a result, the EMG signal data received by the electrodes 106 may also pass through the signal-conditioning electronics 128 and the backing leads 130 prior to passing through the leads 108. In some embodiments, at least some of the signal-conditioning electronics 128 can be positioned within the inner layer 111 and not within the backing material 126 or otherwise coupled to other portions of the gel liner 102 (e.g., the outer layer 103).

Figure 7:
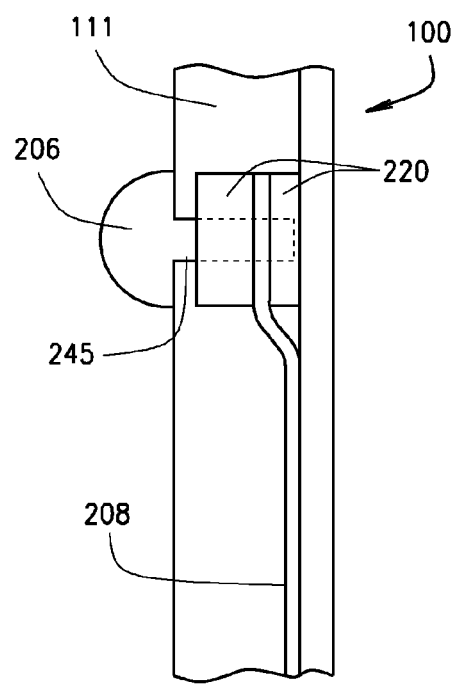
FIG. 7 is an enlarged simplified illustration showing one embodiment of the gel liner.

FIG. 7 illustrates another configuration of electrodes 206 and leads 208. For example, the myoelectric prosthetic control system 100 can include one or more domed electrodes 206. The domed electrodes 206 may be made from a compliant conductive material or the domed electrodes 206 can be made from conductive fabric that is molded over a dome-shaped backing material (not shown).

In one embodiment, the domed electrodes 206 can be coupled to leads 208 via an electrode receptacle 220 (e.g., backing material). The electrode receptacle 220 may be coupled to the outer layer 203 and at least partially retained in positioned by being embedded within the inner layer 111, similar to some previously mentioned embodiments. In one embodiment, one or more leads 208 can be positioned at least partially within the electrode receptacle 220 so that when the domed electrodes 206 are positioned within the electrode receptacles 220, a portion of the domed electrodes 206 can contact the leads 208. Particularly, one or more of the domed electrodes 206 can be made from a relatively rigid material with an extension 245 that can protrude into the electrode receptacle 220 to make contact with one or more leads 208. Further, the domed electrodes 206 can protrude from the inner layer 211 to contact the residual limb 101. As a result, EMG signal data can be transmitted from the domed electrodes 206 to the leads 208.

Figure 8:
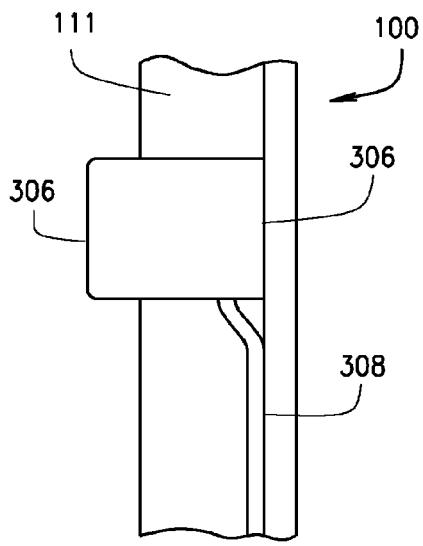
FIG. 8 is an enlarged simplified illustration showing one embodiment of the gel liner.

FIG. 8 illustrates another configuration of one or more electrodes 306 and leads 308. For example, the myoelectric prosthesis control system 100 can employ differently configured electrodes 306. For example, the electrodes 306 can be formed from a compliant conductive material (e.g., a conductive polymer or silicone-containing conductive material) that may be molded over and/or around a non-conductive backing material (not shown). As a result, the compliant conductive material forming the electrodes 306 can extend through the inner layer 111 to contact the residual limb 101. Further, in one embodiment, the compliant conductive material forming the electrodes 306 can serve as the backing material and can be coupled to one or more leads 308 to transfer EMG signal data. For example, at least some of the leads 308 can also be formed of the same or a similar compliant conductive material. In other embodiments, the leads 308 can be coupled to the compliant conductive material of electrodes 306 (e.g., the leads 308 can be made from a different material and attached to the electrodes 306).

Figure 9:
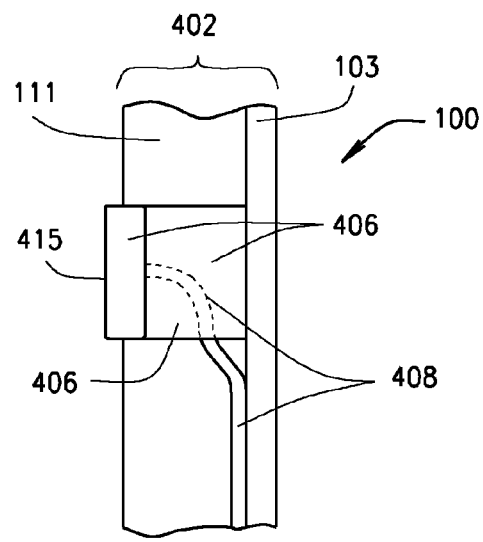
FIG. 9 is an enlarged simplified illustration showing one embodiment of the gel liner.

FIG. 9 illustrates another configuration of one or more electrodes 406 and leads 408. For example, the myoelectric prosthesis control system 100 can employ differently configured electrodes 406. For example, the electrodes 406 can be formed from a pliable conductive material (e.g., a conductive polymer, elastomer, or silicone-containing conductive material) and a pliable non-conductive material. More specifically, the electrodes 406 can be coupled to the inner layer 103 using an adhesive, such as an elastomer-based adhesive, or using mechanical coupling techniques, such as sewing. Similar to some other embodiments, an electrode pole 416 can extend through the inner layer 111 to contact the residual limb 101. In addition, the conductive portion of the electrodes 406 (e.g., the electrode pole 415) can extend through portions of the electrodes 406 made from the non-conductive materials to form leads 408. More specifically, the pliable conductive material can extend to form one or more leads 408 or the pliable conductive material can contact another material that can function as the leads 408. As a result, the pliable conductive material that forms the electrodes poles 415 can conduct EMG signal data to the leads 408 for downstream processing to control movements of the prosthesis 124.

Figure 10:
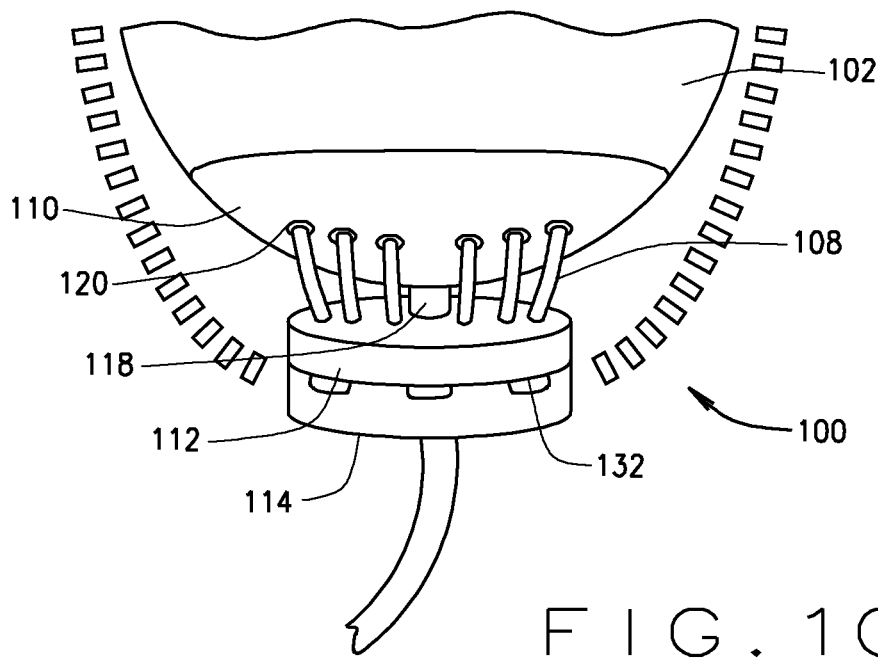
FIG. 10 is a simplified illustration showing an embodiment of a distal end of the gel liner of FIG. 1, including a signal-conditioning electronics module and a distal end connector.

Referring now to FIGS. 1, 5, and 10, the gel liner 102 can include a support member 110 to help facilitate the exit of some or all of the leads 108 from the gel liner 102 and to provide some structural support for the gel liner 102. For example, as shown in FIG. 10, in one embodiment, a plurality of lead apertures 120 can be disposed through the support member 110 so that the leads 108 can extend through the support member 110 and contact portions of the signal-conditioning electronics module 112. In one embodiment, each of the leads 108 can pass through different lead apertures 120 (i.e., one lead 108 per lead aperture 120).

The support member 110 can be coupled to or integral with the gel liner 102. In one embodiment, the support member 110 can be fabricated from a nonconductive material such as a polymer or rubber and can be attached to the gel liner 102. In some embodiments, the support member 110 can be positioned during assembly of the inner layer 111 and positioned adjacent to or at the distal end 105 of the gel liner 102.

After passing through the lead apertures 120, the leads 108 can be coupled to the signal-conditioning electronics module 112. In one embodiment, the leads 108 can be connected to receptacles (not shown) on the signal-conditioning electronics module 112, such as screw terminals (not shown). Furthermore, as previously mentioned, after reaching the signal-conditioning electronics module 112, the EMG signal data can be passed to the socket interface 114. In some embodiments, one or more electrical connections 132 can be positioned between the signal-conditioning electronics module 112 and the socket interface 114. For example, the electrical connections 132 can be formed as complementary magnets that are configured and arranged so that polarities of the magnets can prevent or reduce the chance of incorrect connections.

Figure 11:
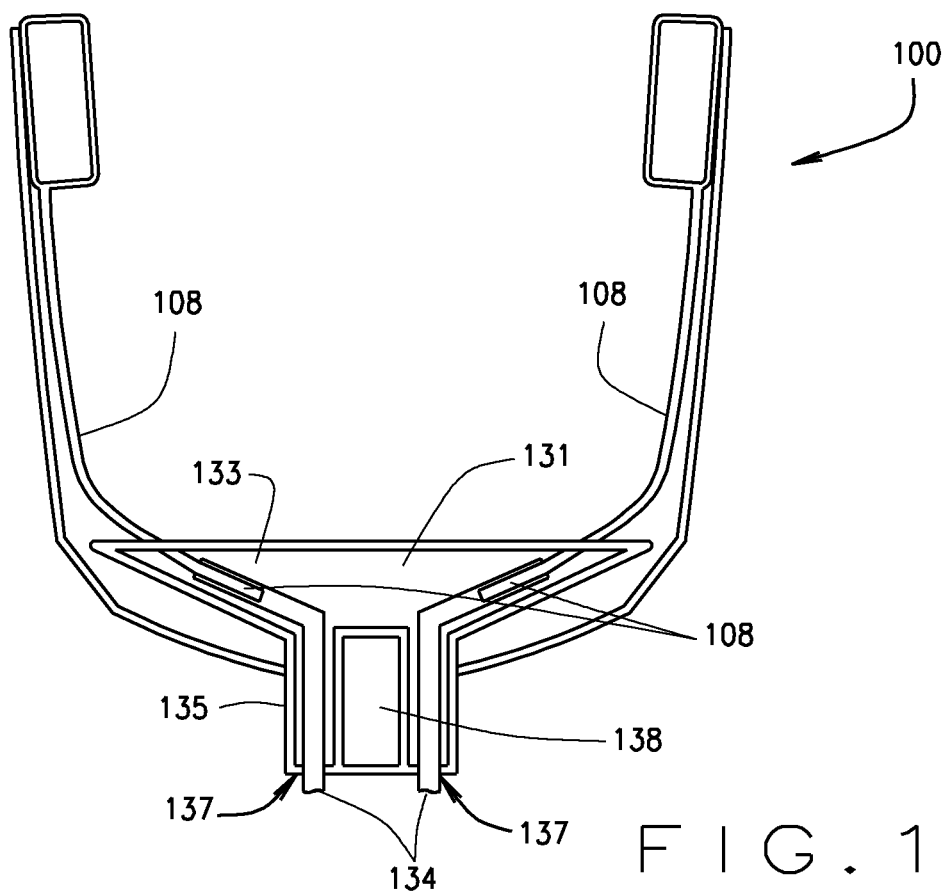
FIG. 11 is a simplified illustration showing one embodiment of a gel liner and a distal end connector.
Figure 12:
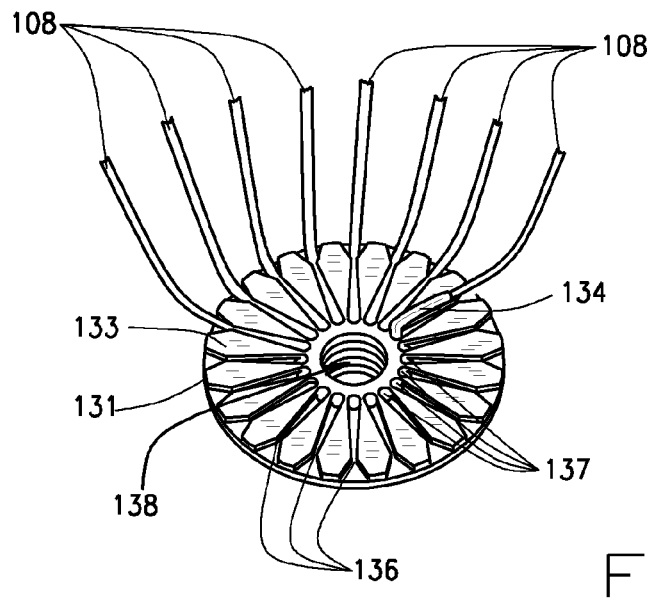
FIG. 12 is a perspective view of the distal end connector and leads of FIG. 11.

Referring now to FIGS. 11 and 12, in one embodiment, the gel liner 102 can include a distal end connector 131. In some embodiments, the gel liner 102 can include the distal end connector 131 in addition to, or in lieu of the support member 110. The distal end connector 131 can include a horizontal flange 133 and a vertical flange 135. In one embodiment, the horizontal flange 133 can be generally planar; however, in some embodiments, the horizontal flange 133 can include a generally angled, curved, or arched configuration. In one embodiment, the distal end connector 131 can be fabricated from a non-conductive material (e.g., a polymer or rubber). Moreover, the distal end connector 131 can be coupled to or integral with the gel liner 102 at the distal end 105 of the gel liner 102. For example, the distal end connector 131 can be coupled to the gel liner 102 so that at least a portion of the distal end connector 131 is positioned within and/or retained in position by the inner layer 111. As a result, at least a portion of the distal end connector 131 (e.g., the vertical flange 135) can extend through the distal end 105 of the gel liner 102.

In one embodiment, the distal end connector 131 can be configured to couple together the gel liner 102 and the signal-conditioning electronics module 112. More specifically, the vertical flange 135 of the distal end connector 131 and the signal-conditioning electronics module 112 can each include one or more threaded apertures 138. As a result, the pass-through screw 118 or other coupling device can be used to couple together the distal end connector 131 and the signal-conditioning electronics module 112.

Moreover, the distal end connector 131 can be configured and arranged so that the leads 108 may extend through the distal end connector 131. More specifically, the distal end connector 131 can include a plurality of member apertures 137. For example, the member apertures 137 can be positioned within and/or disposed through portions of the vertical flange 135. Furthermore, in some embodiments, one or more support conductors 134 can be coupled to and/or supported by the distal end connector 131. The support conductors 134 can exhibit a more rigid composition than the leads 108 so that the connection between the leads 108 and the signal-conditioning electronics module 112 is properly supported. For example, the support conductors 134 may be stiff wire or wire-pin type components that can be coupled to the leads 108. Moreover, the support conductors 134 can be made of a conductive material so that the EMG signal data carried by the leads 108 can be transferred to the signal-conditioning electronics module 112 via the support conductors 134.

Referring to FIG. 12, in one embodiment, the distal end connector 131 includes a plurality of grooves 136. The grooves 136 can be sized and positioned along a surface of the horizontal flange of the distal end connector 131 to receive at least a portion of the support conductors 134 and the leads 108. For example, the leads 108 can be at least partially positioned within the grooves 136 and the support conductors 134 can also be fit within the grooves 136 (e.g., snap-fit within the grooves 136). As a result, the support conductors 134 can retain the leads 108 in place within the grooves 136 and conduct the EMG signal data from the leads 108 to the signal-conditioning electronics module 112 because of the physical contact between the leads 108 and the support conductors 134. More specifically, the support conductors 134 can extend through the member apertures 137 positioned adjacent to the vertical flange 135 to couple the leads 108 and the signal-conditioning electronics module 112. In one embodiment, the support conductors 134 can be coupled to the signal-conditioning electronics module 112 via solder, a conductive adhesive, a mechanical bond, or any other suitable method.

Communication between the signal-conditioning electronics module 112 and the socket interface 114 can begin when the individual dons the prosthesis 124. Contact of the signal-conditioning electronics module 112 and the socket interface 114 may be made when the prosthesis socket 104 is donned over the gel liner 102. As a result, no manual connections need to be made to begin use of the myoelectric prosthesis control system 100.

The signal-conditioning electronics module 112 and the socket interface 114 can be configured to condition the EMG signal data to render it useful for control over movement of the prosthesis 124. For example, the signal-conditioning electronics module 112 and/or the socket interface 114 can be configured as a printed circuit board. Particularly, after conditioning, the EMG signal data can be transmitted to the prosthesis control module 122 via the wire 116 (as shown in FIG. 1), where the conditioned EMG signal data can be used to control movement of the prosthesis 124. For example, conditioning of the EMG signal data may involve buffering, amplification, rectification, and smoothing, and can also depend on the type of control being exerted over the prosthesis 124 (e.g., a pattern recognition-based control algorithm). Alternatively, in some embodiments, other pieces of electronic equipment (not shown) can be used for signal conditioning (including buffering, filtering, amplification, etc.). The other pieces of electronic equipment can be embedded at the site of contact. In this case, the leads 108 carrying the conditioned EMG signal data can exit the gel liner 102 through either the support member 110 (as shown in FIG. 10) or the distal end connector 131 (as shown in FIGS. 11 and 12) and be attached to the signal-conditioning electronics module 112, which is coupled to the socket interface 114.

Figure 13:
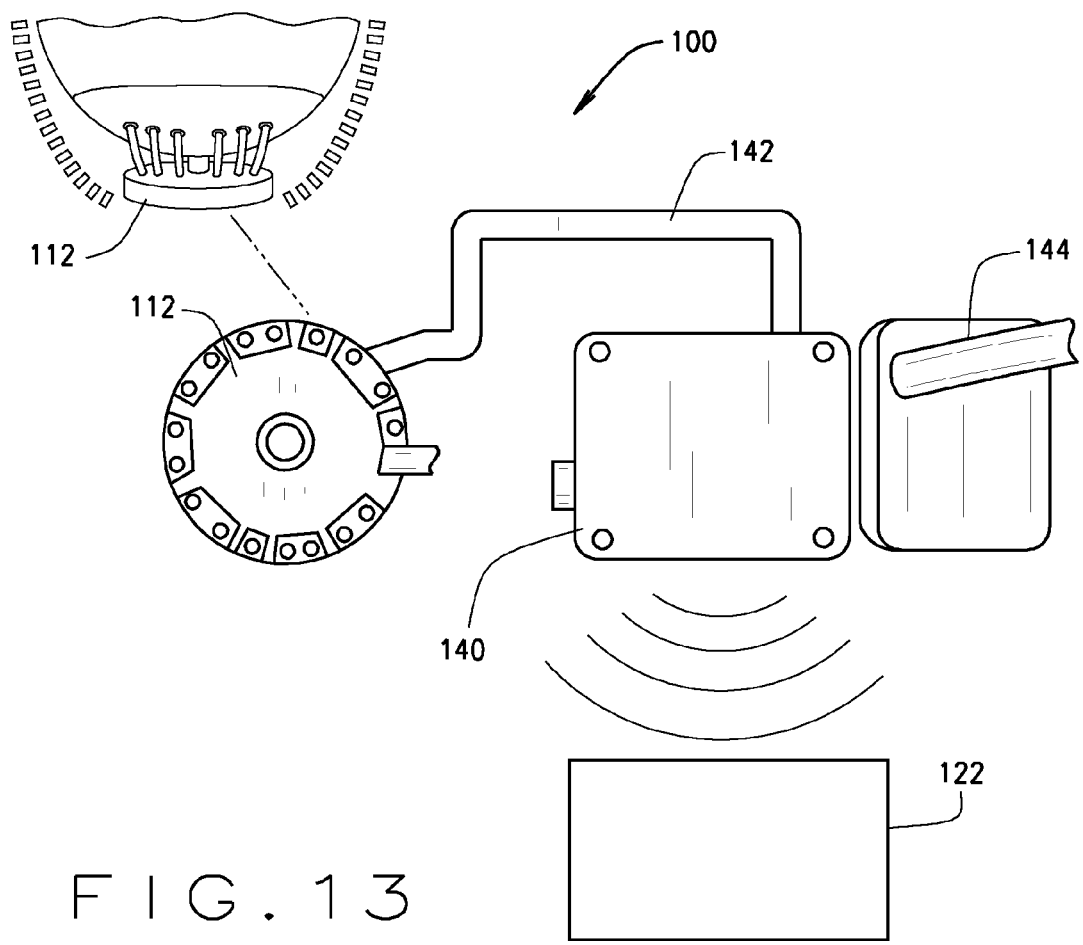
FIG. 13 is a simplified illustration showing one embodiment of a gel liner, signal-conditioning electronics module, and wireless transmitter.

FIG. 13 shows an alternative path for EMG signal transmission through the myoelectric prosthesis control system 100. Particularly, in one embodiment, the EMG signal data can be wireless transmitted to the prosthesis control module 122 or other location. For example, in some embodiments, the signal-conditioning electronics module 112 can be configured to digitize and transfer the EMG signal data to a wireless transmitter module 140. In one embodiment, the signal-conditioning electronics module 112 can be coupled to the wireless transmitter module 140 using one or more wires 142; however, in another embodiment, the wireless transmitter module 140 can be integrated into the signal-conditioning electronics module 112. After receiving the digitized EMG signal data from the signal-conditioning electronics module 112, the wireless transmitter module 140 can broadcast (e.g., via an antennae 144) the EMG signal data as a wireless signal (e.g., using IEEE 802.11 2.4 GHz). Moreover, in some embodiments, the wireless transmitter module 140 can be in operative communication with elements other than the prosthesis control module 122 or the prosthesis 124, such as, but not limited to a remote computing device or other electronic equipment.

In some embodiments, electrodes 106 and electrode poles 115 may be of different sizes, shapes, and thicknesses as required to provide optimal EMG signal detection and signal separation. For example, for an individual with a transradial amputation, one embodiment may include the thickness and diameter of some or all of the electrodes 106 can be about 8 mm and about 12 mm, respectively. However for an individual with a transfemoral amputation, the thickness and diameter of at least some of the electrodes can be between about 5 mm and about 18 mm, respectively. Moreover, in some embodiments, the backing material 126 may be also used to alter the thickness of some of the electrodes 106, as required. Moreover, the size of the electrodes 106 and electrode poles 115 can be optimized both to obtain EMG signal data that is relatively free from cross talk (i.e., record EMG signal data from individual or closely related groups of surface muscles but not from neighboring muscles) and to accommodate the size of the residual limb 101 and the number of electrodes 106 needed.

In addition, some embodiments include custom-manufactured gel liners 102. For example, some or all of the electrodes 106 can be positioned within the gel liner 102 after individualized myotesting (i.e., detection of the site on each muscle that provides the strongest, most independent EMG signal). Conversely, some embodiments include mass-production of gel liners 102 in sizes designed for individuals with specific types and levels of amputation. At least some of the mass-produced gel liners 102 can include electrodes 106 placed in likely useful configurations and locations so that clinicians or technicians can select some or all of the electrodes 106 for use with an individual amputee.

Referring back to FIG. 2, in some embodiments, the gel liners 102 can be mass-produced with an excess number of electrodes 106. As a result, the number and configuration of electrodes 106 used in gathering EMG signal data can be chosen for the individual user by the clinician or technician. For example, some or all of the electrodes 106 can be coupled to the outer layer 103 in a generally grid-like pattern. More specifically, conventional or direct myoelectric control systems rely on isolation of signals from antagonistic muscle pairs (i.e., elbow flexors and elbow extensors) to actuate opposing movements of the prosthesis 124. Other myoelectric control systems (e.g., pattern-recognition controlled prostheses) can receive EMG signal data from multiple areas of the residual limb 101 and do not require specific signals from antagonistic muscle pairs, which enables the use of the grid-like pattern of electrodes 106.

Further, the leads 108 can be routed from the electrodes 106 toward a connector at either the distal end 105 or the proximal end 107 of the gel liner 102 in a generally parallel configuration so that none of the leads 108 contact any of the other leads 108. In some embodiments, the general grid-like pattern of the electrodes 106 and the parallel configuration of the leads 108 can enable the gel liner 102 to be configured for multiple control systems, such as pattern-recognition based control systems or direct control systems. More specifically, the clinician or prosthetist can select some or all of the electrodes 106 to detect EMG signals from the residual limb 101 based on where the EMG signals are most easily detected for each individual.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:
1. A myoelectric prosthesis control system comprising:
 a gel liner detachable from a socket of a prosthesis, the gel liner comprising an inner layer and an outer layer, wherein the inner layer is coated over at least a portion of the outer layer, the gel liner being configured to be worn over a portion of a residual limb, and the gel liner including a distal end and a proximal end;
a plurality of leads fabricated from a conductive fabric;
a plurality of electrodes, each electrode being coupled to a lead, each electrode being at least partially supported by the gel liner and extending through the inner layer to contact the residual limb to detect electromyographic signals;
wherein each lead is at least partially positioned between the inner layer and the outer layer of the gel liner, wherein no portion of any lead protrudes through the outer layer at the location where the lead is coupled to the electrode; and
a distal end connector being coupled to the gel liner adjacent to the distal end of the gel liner, the distal end connector being configured and arranged to receive at least a portion of the plurality of leads.

2. The myoelectric prosthesis control system of claim 1, wherein the plurality of electrodes is fabricated from a compliant conductive material.

3. The myoelectric prosthesis control system of claim 1, wherein the signal-conditioning electronics is electronically coupled to at least one of the plurality of electrodes through the lead for processing electromyographic signal data received by the electrode.

4. The myoelectric prosthesis control system of claim 1, wherein the outer layer comprises fabric and the inner layer comprises a gel material.

5. The myoelectric prosthesis control system of claim 4, wherein the gel material is a thermoplastic elastomer.

6. The myoelectric prosthesis control system of claim 1, wherein distal end connector comprises a horizontal flange having a plurality of grooves that are configured and arranged to receive the plurality of leads.

7. The myoelectric prosthesis control system of claim 1, wherein the distal end connector comprises a plurality of member apertures that are configured and arranged to receive one or more support conductors.

8. The myoelectric prosthesis control system of claim 1, wherein the plurality of electrodes and the plurality of leads are manufactured from different compliant conductive materials.

9. The myoelectric prosthesis control system of claim 1, wherein the inner layer comprises a silicone material.

10. The myoelectric prosthesis control system of claim 1, wherein the inner layer comprises a urethane material.

11. A myoelectric prosthesis control system comprising:
a gel liner detachable from a socket of a prosthesis, the gel liner comprising an inner layer and an outer layer, the gel liner being configured to be worn over a portion of a residual limb by being rolled over the portion of the residual limb, and the gel liner including a distal end and a proximal end;
a plurality of leads fabricated from a conductive fabric;
a plurality of electrodes, each electrode being coupled to a lead, each electrode being at least partially supported by the gel liner and extending from the inner layer to contact the residual limb to detect electromyographic signals;
wherein each lead is at least partially positioned between the inner layer and the outer layer of the gel liner, wherein no portion of any lead protrudes through the outer layer at the location where the lead is coupled to the electrode; and
a distal end connector being coupled to the gel liner adjacent to the distal end of the gel liner, the distal end connector being configured and arranged to receive at least a portion of the plurality of leads.

12. The myoelectric prosthesis control system of claim 11, wherein the plurality of electrodes is fabricated from a compliant conductive material.

13. The myoelectric prosthesis control system of claim 11, wherein the signal-conditioning electronics is electronically coupled to at least one of the plurality of electrodes through the lead for processing electromyographic signal data received by the electrode.

14. The myoelectric prosthesis control system of claim 11, wherein the outer layer comprises fabric and the inner layer comprises a gel material.

15. The myoelectric prosthesis control system of claim 14, wherein the gel material is a thermoplastic elastomer.

16. The myoelectric prosthesis control system of claim 11, wherein the inner layer comprises a silicone material.

17. The myoelectric prosthesis control system of claim 11, wherein the inner layer comprises a urethane material.

18. The myoelectric prosthesis control system of claim 11, wherein distal end connector comprises a horizontal flange having a plurality of grooves that are configured and arranged to receive the plurality of leads.

19. The myoelectric prosthesis control system of claim 11, wherein the distal end connector comprises a plurality of member apertures that are configured and arranged to receive one or more support conductors.

* * * * *